United States Patent [19]

Inui

[11] Patent Number: 4,705,907

[45] Date of Patent: Nov. 10, 1987

[54] PRODUCTION OF LIQUID HYDROCARBON FROM GAS CONTAINING LOWER HYDROCARBON

[75] Inventor: Tomoyuki Inui, 5-43, Hatoyama 1-chome, Uji-shi, Kyoto 611, Japan

[73] Assignees: Showa Shell Sekiyu Kabushiki Kaisha, Tokyo; Tomoyuki Inui, Uji, both of Japan

[21] Appl. No.: 864,779

[22] Filed: May 19, 1986

[30] Foreign Application Priority Data

May 29, 1985 [JP] Japan .................. 60-114259

[51] Int. Cl.$^4$ .............................. C07C 12/02
[52] U.S. Cl. ................... 585/415; 585/417; 585/418; 585/419; 585/421; 585/533; 585/722
[58] Field of Search ............. 585/415, 417, 418, 419, 585/421, 533, 722

[56] References Cited

U.S. PATENT DOCUMENTS

| | | |
|---|---|---|
| 3,960,978 | 6/1976 | Givens et al. |
| 4,120,910 | 10/1978 | Chu .................................. 585/417 |
| 4,260,839 | 4/1981 | Chen . |
| 4,347,394 | 8/1982 | Detz et al. ....................... 585/417 |
| 4,350,835 | 9/1982 | Chester et al. .................. 585/417 |
| 4,490,569 | 12/1984 | Chu et al. ........................ 585/415 |
| 4,497,970 | 2/1985 | Young ............................. 585/417 |

FOREIGN PATENT DOCUMENTS

| | | |
|---|---|---|
| 0050021 | 4/1982 | European Pat. Off. ........... 585/415 |
| 0107875 | 5/1984 | European Pat. Off. ........... 585/417 |
| 0107876 | 5/1984 | European Pat. Off. ........... 585/417 |
| 0107877 | 5/1984 | European Pat. Off. ........... 585/417 |
| 0129239 | 12/1984 | European Pat. Off. . |
| 3139355 | 6/1982 | Fed. Rep. of Germany . |
| 2240904 | 3/1975 | France . |
| 236997 | 2/1978 | France . |

OTHER PUBLICATIONS

Patent Abstracts of Japan, vol. 9 #125, Inui.
European Search Report.

*Primary Examiner*—Curtis R. Davis
*Attorney, Agent, or Firm*—Ladas & Parry

[57] ABSTRACT

Liquid hydrocarbon is prepared with high efficiency from hydrocarbon gas containing $C_2$–$C_5$ paraffinic hydrocarbons and/or $C_2$–$C_5$ olefinic hydrocarbons by bringing the gas into contact with a metallo-silicate catalyst having the following chemical composition in mol %:

Si/Me:15–3500
$OH^-/SiO_2$:0.3–1.0
$H_2O/SiO_2$:30–100
R/(R+alkali metal):0.05–0.15
$NaCl/H_2O$:0.01–0.06 where R is quaternary alkylammonium cation, alkali metal is Na or K, Me is metal ion of B, Al, Ti, V, Cr, Mn, Fe, Co, Ni, Zn, Ga, Ge, Zr, Mo, W, La or Sc, and having the following acidity per g of catalyst:
total acid 0.1–4.5 milli-equivalent
strong acid 0.05–2.0 milli-equivalent
weak acid 0.05–3.0 milli-equivalent.

8 Claims, 4 Drawing Figures

PRODUCTION OF LIQUID HYDROCARBON FROM GAS CONTAINING LOWER HYDROCARBON

The present invention relates to production of liquid hydrocarbon from gas containing lower hydrocarbons. More particularly, this invention pertains to production of liquid hydrocarbon from gas containing paraffinic hydrocarbons of $C_2-C_5$, olefinic hydrocarbons of $C_2-C_5$ or mixtures thereof.

Recently, developement of utilization of heavy oils have been desired, because heavy oils become excess due to energy conservation of heavy oil fuels and conversion to coal and atomic energy. Thermal decomposition or catalytic cracking of heavy oils hardly yields selectively gasoline fraction, and a large amount of gas hydrocarbons, particularly olefins is produced under higher decomposition rate. Conversion of the hydrocarbon gas into liquid ones will produce added value and turn cracking operation in its favor, no matter what distribution of hydrocarbons may be in decomposition of heavy oils.

Conversion of hydrocarbon gas into liquid ones comprises successive or competitive reactions of polymerization, isomerization, disproportionation, decomposition, alkylation, cyclization and dehydrogenation, all of which are based on carbonium ion mechanism. Acidity gives great influence thereon. There will be strength and amount of acid suitable therefor. Selectivity of reaction products is controlled by balances between acidity and amount of catalyst and between hydrogenation and dehydrogenation activities of the catalyst.

The present metallo-silicate catalyst has metals uniformly distributed in its skeleton. Acidity or acid content and hydrogenation/dehydrogenation activities vary depending on metals and Si/Me ratio. Dehydrogenation capacity is large when Me is Zn, Cr or Mn, but hydrogenation capacity is large when Me is Ni or Co. Reaction product is greatly influenced by balance against acidity of catalyst. An amount of aromatic hydrocarbons in liquid hydrocarbons of $C_5$ or more is controlled by acidity of catalyst and reaction conditions. Condensation of aromatic hydrocarbons produced and deposition of carbon produced through carbonization bring about deactivation of catalyst. Longer life of catalyst is expected by controlling production and decomposition of aromatic hydrocarbons.

After extensive study, the present inventor has found that conversion of gas containing hydrocarbons of $C_2-C_5$ into liquid ones is effected with high efficiency by bringing the gas into contact with a catalyst of metallo-silicate having specific pentacyl form and specific acidity under specific conditions.

According to the present invention, gas containing paraffinic hydrocarbons of $C_2-C_5$, olefinic hydrocarbons of $C_2-C_5$ or mixtures thereof is brought into contact with a metallo-silicate catalyst defined below under such conditions as 220°–550° C., atmospheric pressure to 100 Kg/cm$^2$, and 300–15000 hr$^{-1}$ of space velocity until liquid olefin is obtained, said catalyst having the following chemical composition in mol % ratio:

Si/Me:15–3500
OH$^-$/SiO$_2$:0.3–1.0
H$_2$O/SiO$_2$:30–100
R/(R+alkali metal):0.05–0.15
NaCl/H$_2$O:0.01–0.06 wherein R is a quaternary ammonium, cation,
alkali metal is sodium or potassium,
Me is one of B, Al, Ti, V, Cr, Mn, Fe, Co, Ni, Zn, Ga, Ge, Zr, Mo, W, La and Sc
and having the following acidity per g of catalyst:
total acid 0.1–4.5 milli-equivalent,
strong acid 0.05–2.0 milli-equivalent, and
weak acid 0.05–3.0 milli-equivalent.

Followings are conditions in order to decrease an amount of aromatic hydrocarbons in the liquid hydrocarbon:
Acidity per g of catalyst:
    total acid 0.1–3.1 milli-equivalent or
    strong acid 0.05–0.6 milli-equivalent or
    weak acid 0.05–2.5 milli-equivalent
Temperature:
    260°–400° C., preferably 300°–340° C.
Pressure:
    atmospheric pressure-100 Kg/cm$^2$,
    preferably up to 30 Kg/cm$^2$
Space velocity:
    500–15000 hr$^{-1}$, preferably 500–4000 hr$^{-1}$.

Followings are conditions in order to increase an amount of aromatic hydrocarbons in the liquid hydrocarbon:
Acidity per g of catalyst:
    total acid 0.3–0.9 milli-equivalent,
    strong acid 0.2–0.5 milli-equivalent and
    weak acid 0.1–0.5 milli-equivalent
Temperature:
    300°–550° C., preferably 320°–500° C.
Pressure:
    atmospheric pressure-50 Kg/cm$^2$,
    preferably up to 30 Kg/cm$^2$
Space velocity:
    500–15000 hr$^{-1}$, preferably 500–4000 hr$^{-1}$.

In the accompanying drawings.

Figure 1:
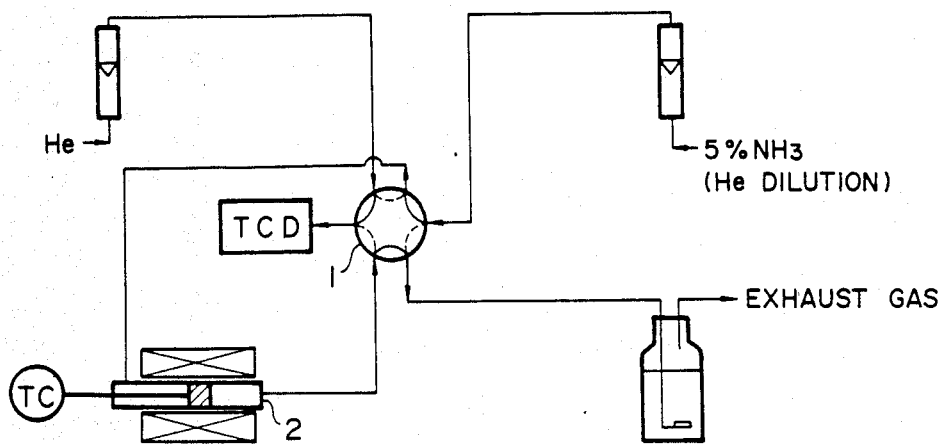
FIG. 1 is an apparatus to observe acidity of a catalyst.

Feed gas used in the present invention contains $C_2-C_5$ paraffinic hydrocarbons, $C_2-C_5$ olefinic hydrocarbons or mixtures thereof. Additionally the feed gas may contain the other hydrocarbons, water, inert gas such as nitrogen, etc. The other hydrocarbons mentioned above are gas originated from thermofor catalytic cracking process (.T.C.C. process), fluid catalytic cracking process (F.C.C. process) or the like, $C_3$-dry gas, $C_4$-mixed gas originated from unsaturated gas plants, gas produced from coking or gas produced from thermal decomposition.

The present catalyst is produced by any processes disclosed in Japanese patent application Nos. 136715/1980 and 173234/1982 and Japanese patent publication No. 12135/1985. This is, a process is applied, which includes at least one of the three steps defined below. The first step is to add at given rates the solution (A) defined below and aqueous silicate solution (B) to aqueous ion modifier (NaCl) solution (C), respectively, controlling the respective addition rates so that changes in concentrations of the components in respective solutions are made small. In this step, part of the (C) solution is added to the (A) solution, while nitrogen-containing organic cations, inorganic acids and alkali hydride are added to the solution (C). The solution (A) contains metal salts defined below, nitrogen-containing organic cations and inorganic acids:

Si/Me:15-3500 mol %
OH$^-$/SiO$_2$:0.3-1.0 mol %
H$_2$O/SiO$_2$:30-100 mol %
R/(R+alkali metal):0.05-0.15 mol % and
NaCl/H$_2$O:0.01-0.06 mol % where R is a quaternary alkyl ammonium cation, alkali metal is sodium or potassium, Me is a metal atom of B, Al, Ti, V, Cr, Mn, Fe, Co, Ni, Zn, Ga, Ge, Zr, Mo, W, La or Sc.

The second step is grinding the gel mixture produced in the first step above. The third step is hydrothermal synthesis by heating with a given rate the gel mixture obtained in the second step from room temperature to 150°-190° C. and then up to 220° C. with a give rate or an exponential rate.

Preferred Me in Si/Me is Al, Fe, Cr, Zn, Ni, Mn, W, B, Ti, Ga, Mo or La when liquid hydrocarbon containing some aromatic hydrocarbons is produced from gas comprising mainly C$_4$ hydrocarbon, and Fe, B, Zn, Ni or W when liquid hydrocarbons containing much aromatic hydrocarbons is produced from gas comprising mainly C$_3$ hydrocarbon.

The present catalyst may carry Pt, Pd and/or Rh thereon by immersion or ion-exchange.

One of preparations of the catalyst is shown below.

Composition of the starting solution for Si/Al (atomic ratio)=3200

| Solution A | |
|---|---|
| Al$_2$(SO$_4$)$_3$.17H$_2$O | 0.034 g |
| Tetrapropylammonium bromide (TPAB) | 5.720 g |
| NaCl | 11.950 g |
| H$_2$O | 60.000 g |
| H$_2$SO$_4$ | 6.200 g |
| Solution B | |
| Water glass* | 69.000 g |
| H$_2$O | 45.000 g |
| *SiO$_2$ 28.9% Na$_2$O 9.3% | |
| Solution C | |
| TPAB | 2.160 g |
| NaCl | 40.590 g |
| NaOH | 2.390 g |
| H$_2$O | 208.000 g |
| H$_2$SO$_4$ | 1.800 g |

When, for example, Me is Zr, sulfate, nitrate, chloride, carbonate or halide of Zr is used in place of the Al$_2$(SO$_4$)$_3$.17H$_2$O, taking Si/Me=3200 into account.

The solutions (A) and (B) are added through microfeeders to the solution (C) so that pH of the solution is maintained 9-11. Period of time required for this addition is about 10 minutes. After gel is formed, centrifugation is applied thereto to separate mother liquor from solid. Solid separated is ground for one hour in a motar and then combined with the mother liquor above.

The mixture obtained is heated in an autoclave with stirring to 160° C. over 90 minutes and then straight up to 210° C. over 250 minutes. The product is washed with distilled water (about 60 ml) 8 times, dried and then calcined at 540° C. for 3.5 hours in an air stream (flow velocity=100 ml/min). After calcining is over, immersion with stirring at 80° C. for one hour is made twice in aqueous NH$_4$NO$_3$ solution (1 mol/l) until ion-exchange is carried out. After the product is washed three times with distilled water (60 ml), calcination at 540° C. in an air-stream(flow velocity=100 ml/min) is made for 3.5 hours.

For reference, one of conventional processes is shown as follows:

Starting solutions for Si/Al=3200

| Solution A' | |
|---|---|
| Al$_2$(SO$_4$)$_3$.17H$_2$O | 0.034 g |
| TPAB | 7.530 g |
| H$_2$O | 60.000 g |
| H$_2$SO$_4$ | 6.200 g |
| Solution B' | |
| Water glass* | 69.000 g |
| H$_2$O | 45.00 g |
| Solution C' | |
| NaCl | 26.270 g |
| H$_2$O | 104.000 g |

*the same as in solution B

The solutions (A') and (B') are dropped to the solution (C') until the components are well mixed. Then, the above steps are repeated to prepare alumino-silicate catalyst.

Electron microscopic observation under scanning MSM4C-102 of crystals of the catalyst prepared by the present invention reveals that each crystal particle looks secondary one made of small plate crystals, except secondary one having the ammonoidia shape when Me is Ga.

BET surface area by Shimadzu TG-20 is 288 m$^2$/g, when Me is Al (ZSM-5),± about 60 m$^2$/g, i.e., 223 m$^2$/g for Ti and 350 m$^2$/g for Zr. There are some differences with respect to pore structures. Highly crystallization is observed in the present catalyst in view of that an amorphous silicaalumina has the surface area of 10 m$^2$/g, at most. Crystals when atomic ratios of Si/Zr are 800 and 400 resemble that of typical ZSM-5.

Acidity or acid content of the catalyst is observed by means of the apparatus of FIG. 1, where an amount of ammonia adsorbed on a given catalyst is measured. Conditions are amount of catalyst: 500 mg
pretreatment for removing ammonia: He 50 ml/min 600° C. 30 min
adsorption of ammonia: 5% ammonia gas diluted with helium, 100 ml/min., room temperature, 30 min.
desorption of ammonia: He 50 ml/min. 80°-600° C. (raising rate: 10° C./min.
detector: thermal conductivity detector ("Hitachi"063 gas chromatograph)
reaction tube: quartz tube, inner diameter 6 mm Result Acidity is decided by comparison of peak area of a sample with standard one based on known acidity.

Figure 2:
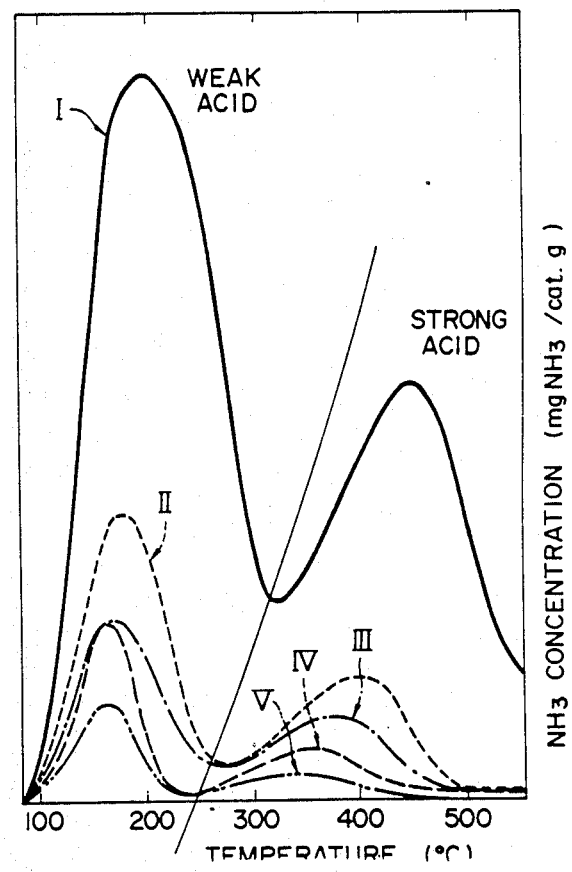
FIG. 2 is a diagram where acidities of the present catalysts having various Se/Me ratios are shown.

In FIG. 2, lines I-V are acidities of catalysts where Si/Al=40, Si/Al-200, Si/Al=400, Si/Al=1200 and Si/Al=3200, respectively.

Figure 3:
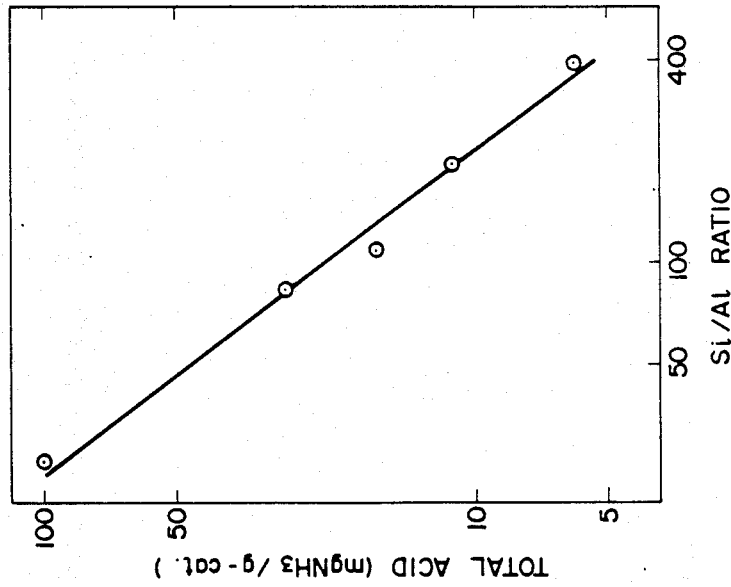
FIG. 3 is a diagram showing relation between Si/Al mol ratio of metallo-silicate catalyst and total acid (mg NH$_3$/g catalyst)

Relation between Si/Al mol ratio and total acid (mg NH$_3$/g-catalyst) is shown in FIG. 3.

Figure 4:
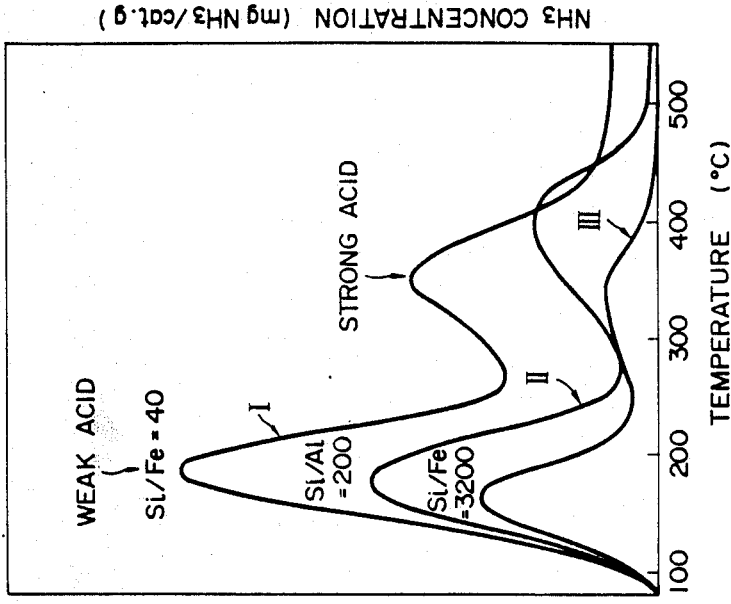
FIG. 4 is TPD spectrum diagram of an iron-metallosilicate catalyst.

In FIG. 4 of TPD spectrum diagram, lines I-III are for Si/Fe=40, Si/Fe=200 and Si/Fe=3200, respectively.

As is disclosed above, liquid hydrocarbon is prepared with high yield from hydrocarbon gas without thermal decomposition thereof. An amount of aromatic hydrocarbons in liquid hydrocarbon obtained is easily controlled by changing metals and acidity of the present metallo-silicate catalyst as well as reaction conditions. Feed gas may be charged with high speed, since the catalyst is highly active. Easy controlling of reaction temperature is made without doing any harm on high space velocity as well as reaction rate by selecting a combination of the catalyst and reaction conditions, even in a large scale apparatus, although reaction heat is liable to accumulate to cause temperature rising and run-away in such an apparatus. The present metallo-silicate catalyst, even in the form of matrix with inert solid such as carriers, is able to easily handle as same as a single catalyst.

The following example illustrates the present invention.

EXAMPLE

A conventional tubular flow reactor (2) (inner diameter 6 mm) in which 214 mg of a metallo-silicate catalyst had been packed (packed volume 0.348 ml), said catalyst being 7–15 mesh in size after the catalyst prepared as above was shaped into tablets (density 1.0 g/cm$^3$). Feed gas was charged as it is or after being diluted with nitrogen gas under space velocity of 900 hr$^{-1}$ and reaction was effected at 220°–550° C. Components in the conversion gas were assayed by meas of TCD gas chromatograph (1). Test results are shown in Tables 1–4. In the tables, a conversion rate is shown by mol % of the feed gas consumed in the reaction.

(1) Influence of catalysts

Butene-butane mixed gas was fed on various metallo-silicate catalysts to observe yields of liquid hydrocarbon. Result is shown in Tables 1 and 2.

Feed gas composition:
$C_3$ 0.5 wt.%, $C_4$ 36.1 wt.%, $C_4'$ 51.9 wt.%, $C_5+$ 11.5 wt.%.

The tables show that gasoline yields i.e., total % of $C_5+$ hydrocarbons and aromatic hydrocarbons, are large when Me is Zn, Fe, Al, Cr, Mn, Ni, Ti, Ga, Mo, W, B or La and small when Me is V, Co, Sc, Ge and Zr, and that atomic ratios of Si/Me in the catalysts do not give some influence on the gasoline yields.

(2) Influence of feed gas

Table 3 shows influence of feed gases, i.e., thermal decomposition gas (BBF) mainly comprising butene and butane, butene gas and propylene gas on gasoline yield.

The table shows that butene gas and decomposition gas containing butene and butane as the main component do not give some influence under the reaction conditions properly selected.

Example 29 which is shown for reference, where Example 28 was repeated except a metallo-silicate catalyst having no acidity was used. No gasoline was produced.

(3) Influence of reactions

Catalysts used:
*1. Alumino-silicate catalyst (Si/Al=40, amount of weak acid=45.35, amount of strong acid=26.67, amount of total acid=72.02)/α-alumina/-silica=44:44:12 (weight %),
*2. Alternate stack of the same alumino-silicate as 1 above (150 ml) and α-alumina (50 ml),
*3. Cartridge packed with alumino-silicate catalyst (mentioned above).

Propylene gas or butene-butane mixed gas (BBF) were fed on the catalysts above or mixtures thereof.

Yields of $C_5+$ hydrocarbons and space time yields (STY) of the olefinic hydrocarbons are shown in Table 4. The table shows that high gasoline yield and high STY are obtained no matter what the catalysts are placed in a reactor.

TABLE 1

(Feed gas; BBF, SV 900 hr$^{-1}$, Atmospheric pressure)

| | | Exp. No. | 1 | 2 | 3 | 4 | 5 | 6 | 7 | 8 |
|---|---|---|---|---|---|---|---|---|---|---|
| | | Si/Me | Si/Al 40 | Si/Al 3200 | Si/Fe 3200 | Si/Cr 3200 | Si/Zn 3200 | Si/Ni 3200 | Si/Mn 3200 | Si/V 3200 |
| Acidity | Amount of weak acid | | | | | | | | | |
| | | mgNH$_3$/cat.g | 45.35 | 2.72 | 1.75 | 6.68 | 7.02 | 4.81 | 6.73 | 7.95 |
| | | mmeq./cat.g | 2.67 | 0.16 | 0.10 | 0.39 | 0.41 | 0.28 | 0.40 | 0.47 |
| | Amount of strong acid | | | | | | | | | |
| | | mgNH$_3$/cat.g | 26.67 | 1.56 | 3.52 | 6.86 | 4.73 | 4.98 | 6.66 | 8.53 |
| | | mmeq./cat.g | 1.57 | 0.09 | 0.21 | 0.40 | 0.28 | 0.29 | 0.39 | 0.50 |
| | Amount of total acid | | | | | | | | | |
| | | mgNH$_3$/cat.g | 72.02 | 4.28 | 5.27 | 13.54 | 11.75 | 9.79 | 13.39 | 16.48 |
| | | mmeq./cat.g | 4.24 | 0.25 | 0.31 | 0.79 | 0.69 | 0.57 | 0.79 | 0.97 |
| B | A | C-wt % | | | | | | | | |
| | | $C_5+$ | 29.37 | 31.31 | 33.46 | 28.51 | 35.82 | 19.88 | — | 3.36 |
| | | Arom* | 3.65 | 1.98 | 1.14 | 0.77 | 3.06 | 0.97 | — | 0.15 |
| | | Gasoline | 33.02 | 32.36 | 34.60 | 29.28 | 38.88 | 20.85 | 25.84 | 3.51 |
| | | $C_4-$ | 12.02 | 25.17 | 17.84 | 5.24 | 3.62 | 35.77 | 26.87 | 55.13 |
| C | A | C-wt % | | | | | | | | |
| | | $C_5+$ | 24.29 | 34.78 | 34.34 | 34.24 | 27.91 | 35.05 | — | 14.96 |
| | | Arom* | 8.49 | 3.57 | 3.84 | 2.49 | 6.51 | 2.53 | — | 1.23 |
| | | Gasoline | 32.78 | 38.27 | 38.18 | 36.73 | 34.42 | 37.58 | 35.89 | 16.19 |
| | | $C_4-$ | 6.26 | 17.33 | 13.84 | 17.45 | 1.66 | 17.45 | 18.52 | 41.59 |
| D | A | C-wt % | | | | | | | | |
| | | $C_5+$ | 17.00 | 31.58 | 30.58 | 31.12 | — | 31.83 | — | 21.45 |
| | | Arom* | 13.84 | 3.56 | 5.07 | 3.34 | — | 3.30 | — | 1.01 |
| | | Gasoline | 30.84 | 35.04 | 35.65 | 34.46 | — | 35.13 | 36.71 | 22.46 |
| | | $C_4-$ | 4.44 | 16.61 | 16.86 | 19.56 | — | 20.31 | 20.15 | 34.65 |
| | | | 9 | 10 | 11 | 12 | 13 | 14 | 15 | 16 |

TABLE 1-continued (Feed gas; BBF, SV 900 hr$^{-1}$, Atmospheric pressure)

| | Exp. No.<br>Si/Me | Si/Co<br>3200 | Si/Zr<br>3200 | Si/Ti<br>3200 | Si/Ga<br>16 | Si/Ge<br>32 | Si/Mo<br>3200 | Si/La<br>3200 | Si/Sc<br>3200 |
|---|---|---|---|---|---|---|---|---|---|
| | Acidity Amount of weak acid | | | | | | | | |
| | mgNH$_3$/cat.g | 10.79 | 6.71 | 1.36 | 16.83 | 41.82 | 3.22 | 1.53 | 12.41 |
| | mmeq./cat.g | 0.63 | 0.39 | 0.06 | 0.99 | 2.46 | 0.19 | 0.09 | 0.73 |
| | Amount of strong acid | | | | | | | | |
| | mgNH$_3$/cat.g | 5.08 | 9.43 | 0.51 | 2.72 | 9.52 | 2.97 | 1.53 | 4.76 |
| | mmeq./cat.g | 0.30 | 0.55 | 0.05 | 0.16 | 0.56 | 0.17 | 0.09 | 0.28 |
| | Amount of total acid | | | | | | | | |
| | mgNH$_3$/cat.g | 15.87 | 16.14 | 1.87 | 19.55 | 51.34 | 6.19 | 3.06 | 17.17 |
| | mmeq./cat.g | 0.93 | 0.94 | 0.11 | 1.15 | 3.02 | 0.36 | 0.18 | 1.01 |
| E A | C-wt % | | | | | | | | |
| | C$_5$+ | 1.40 | 3.90 | 35.42 | 30.22 | 3.01 | 29.87 | 34.66 | 3.07 |
| | Arom* | — | 0.24 | 1.44 | 1.06 | 0.14 | 0.89 | 1.37 | 0.17 |
| | Gasoline | 1.40 | 4.20 | 36.84 | 31.28 | 3.15 | 30.76 | 36.03 | 3.24 |
| | C$_4$− | 56.65 | 54.44 | 28.94 | 8.23 | 54.71 | 17.69 | 28.03 | 57.20 |
| C A | C-wt % | | | | | | | | |
| | C$_5$+ | 2.70 | 13.10 | 41.55 | 37.40 | 15.54 | 35.92 | 41.78 | 8.95 |
| | Arom* | — | 0.83 | 5.26 | 3.54 | 1.11 | 3.14 | 5.11 | 1.07 |
| | Gasoline | 2.70 | 13.93 | 36.29 | 33.86 | 14.43 | 32.78 | 36.67 | 7.88 |
| | C$_4$− | 55.49 | 44.08 | 12.63 | 7.15 | 44.70 | 15.43 | 15.93 | 38.24 |
| D A | C-wt % | | | | | | | | |
| | C$_5$+ | 7.45 | 19.75 | 40.69 | 35.01 | 21.90 | 32.11 | 39.02 | 15.57 |
| | Arom* | — | 0.94 | 8.36 | 4.32 | 1.24 | 3.23 | 7.89 | 1.33 |
| | Gasoline | 7.45 | 10.69 | 32.33 | 30.69 | 20.66 | 28.88 | 31.13 | 14.24 |
| | C$_4$− | 51.67 | 37.70 | 16.76 | 8.04 | 42.73 | 17.38 | 18.66 | 30.48 |

Notes:
*Aromatic hydrocarbons
A Hydrocarbon distribution
B Reaction temperature at 300° C.
C Reaction temperature at 330° C.
D Reaction temperature at 360° C.
E Reaction temperature at 295° C.

TABLE 2

(Feed gas: Propylene, SV 900 hr$^{-1}$; Atmospheric pressure)

| | Exp. No.<br>Si/Me | 17<br>Si/Al<br>40 | 18<br>Si/Fe<br>3200 | 19<br>Si/B<br>3200 | 20<br>Si/W<br>3200 | 21<br>Si/Zn<br>3200 | 22<br>Si/Ni<br>3200 | 23<br>Si/Co<br>3200 |
|---|---|---|---|---|---|---|---|---|
| | Acidity Amount of weak acid | | | | | | | |
| | mgNH$_3$/cat.g | 45.35 | 1.75 | 7.24 | 6.14 | 7.02 | 4.81 | 10.79 |
| | mmeq./cat.g | 2.67 | 0.10 | 0.43 | 0.36 | 0.41 | 0.28 | 0.63 |
| | Amount of strong acid | | | | | | | |
| | mgNH$_3$/cat.g | 26.67 | 3.52 | 7.51 | 8.26 | 4.73 | 4.98 | 5.08 |
| | mmeq./cat.g | 1.57 | 0.21 | 0.44 | 0.49 | 0.28 | 0.29 | 0.30 |
| | Amount of total acid | | | | | | | |
| | mgNH$_3$/cat.g | 72.02 | 5.27 | 14.75 | 14.40 | 11.75 | 9.79 | 15.87 |
| | mmeq./cat.g | 4.24 | 0.31 | 0.87 | 0.85 | 0.69 | 0.57 | 0.93 |
| B A | C-wt % | | | | | | | |
| | C$_5$+ | 62.44 | 54.29 | 50.71 | 45.67 | 47.29 | 70.44 | 16.21 |
| | Arom* | 12.98 | 45.51 | 49.20 | 54.25 | 52.64 | 7.84 | 1.34 |
| | Gasoline | 75.42 | 99.80 | 99.91 | 99.92 | 99.93 | 78.28 | 17.55 |
| | C$_4$− | 6.96 | 0.16 | 0.06 | 0.05 | 0.05 | 18.64 | 82.32 |
| C A | C-wt % | | | | | | | |
| | C$_5$+ | 37.42 | 60.00 | 50.17 | 58.57 | 38.93 | 51.63 | 43.75 |
| | Arom* | 16.81 | 4.84 | 49.69 | 40.39 | 60.94 | 47.98 | 3.46 |
| | Gasoline | 54.23 | 64.84 | 99.86 | 98.96 | 99.87 | 99.61 | 47.21 |
| | C$_4$− | 3.42 | 25.53 | 0.08 | 0.55 | 0.06 | 0.30 | 52.34 |
| D A | C-wt % | | | | | | | |
| | C$_5$+ | 24.05 | | | | — | — | — |
| | Arom* | 23.26 | | | | | | |
| | Gasoline | 47.31 | | | | — | — | — |

TABLE 2-continued (Feed gas: Propylene, SV 900 hr$^{-1}$: Atmospheric pressure)

| Exp. No. Si/Me | 17 Si/Al 40 | 18 Si/Fe 3200 | 19 Si/B 3200 | 20 Si/W 3200 | 21 Si/Zn 3200 | 22 Si/Ni 3200 | 23 Si/Co 3200 |
|---|---|---|---|---|---|---|---|
| $C_4^-$ |  | 2.36 |  |  |  |  |  |

Notes:
*Aromatic hydrocarbons
A Hydrocarbon distribution
B Reaction temperature 300° C.
C Reaction temperature 330° C.
D Reaction temperature 360° C.

TABLE 3

(Under pressure)

| Exp. No. Si/Me | Feed gas | No. 24 BBF Si/Al 40 | No. 25 BBF Si/Fe 3200 | No. 26 Propylene Si/Al 40 | No. 27 Butene Si/Al 40 | No. 28 BBF Si/Fe 800 | No. 29 BBF Si/Fe 800 |
|---|---|---|---|---|---|---|---|
| Acidity | Amount of weak acid |  |  |  |  |  |  |
|  | mgNH$_3$/cat.g | 45.35 | 1.75 | 45.35 | 45.35 | 45.35 | No acidity |
|  | mmeq./cat.g | 2.67 | 0.10 | 2.67 | 2.67 | 2.67 | 0 |
|  | Amount of strong acid |  |  |  |  |  |  |
|  | mgNH$_3$/cat.g | 26.67 | 3.52 | 26.76 | 26.76 | 26.76 |  |
|  | mmeq./cat.g | 1.57 | 0.20 | 1.57 | 1.57 | 1.57 | 0 |
|  | Amount of total acid |  |  |  |  |  |  |
|  | mgNH$_3$/cat.g | 72.02 | 5.27 | 72.02 | 72.02 | 72.02 |  |
|  | mmeq./cat.g | 4.24 | 0.30 | 4.24 | 4.24 | 4.24 | 0 |
| Reaction condition | Temp. °C. | 300 | 400 | 280 | 260 | 330 | 410 |
|  | Pressure Kg/cm$^2$ | 10 | 20 | 10 | 10 | 10 | 10 |
|  | GHSV hr$^{-1}$ | 500 | 500 | 13800 | 1000 | 850 | 1000 |
|  | Ratio (Vol) of dilution with nitrogen | 4 | 1 | 1 | 2 | 2.3 | 1 |
| C-wt % | C$_5^+$ Hydrocarbon | 23.1 | 34.4 | 54.3 | 32.9 | 37.4 | 0 |
|  | Aromatics | — | — | ≧44 | 0 | 4.3 | 0 |

TABLE 4

| Feed material | Exp. No. 30 BBF | Exp. No. 31 BBF | Exp. No. 32 BBF | Exp. No. 33 BBF | Exp. No. 34 Propylene | Exp. No. 35 Propylene |
|---|---|---|---|---|---|---|
| Reaction form | Bench scale | Bench scale | Bench scale | Bench scale | Small scale (under pressure) | Small scale (under pressure) |
| Catalyst | 1 | 2 | 3 | 3 | Fe—silicate catalyst Si/Fe = 800 10 ml | Fe—silicate catalyst Si/Fe = 3200 3 ml |
| Reaction condition — Temperature (°C.) | X: 360° C. Y: 360° C. | X: 360–380° C. Y: 350° C. | 365–380° C. | 370–390° C. | 340° C. | 330° C. |
| Pressure (Kg/cm$^2$) | 10 | 10 | 10 | 20 | 15 | 1 |
| LHSV (hr$^{-1}$) | 1.59 | 3.09 | 3.73 | 3.74 | 3.6 | 3.24 |
| N$_2$/Feed | 1.65 | 1.84 | 0.42 | 0.69 | 2 | 0 |
| C$_5^+$ Hydrocarbons (C-wt %) | 39.9 | 46.4 | 39.6 | 36.3 | 60.1 | 99.86 |
| Reaction yield of converted olefins (%) | 91.9 | 88.8 | 83.8 | 81.5 | 97.6 | 99.90 |

Note
1 Two reactors X and Y are arranged in series where X: packed with *1 (200 ml) and Y: packed with *2 (200 ml).
2 Two reactors X and Y are arranged in series where X: packed with *1 (200 ml) and Y: packed with *3 (100 ml).
3 Single reactor packed with *3 (100 ml).

I claim:

1. A process for preparing liquid hydrocarbon from lower hydrocarbon gas which comprises bringing feed gas containing $C_2$-$C_5$ paraffinic hydrocarbons, $C_2$-$C_5$ olefinic hydrocarbons or mixtures thereof into contact with a metallo-silicate catalyst (Si/Me) wherein the atomic ratio of Si/Me is 15-3500 and Me is selected from the group consisting of B, Al, Ti, Zr, Ge, La, Mn, Cr, Sc, V, Fe, W, Mo, Co, Zn, Ga and Ni, and the acidity per g of catalyst is total acid: 0.1-4.5 milli-equivalent
strong acid: 0.05-2.0 milli-equivalent and
weak acid: 0.05-3.0 milli-equivalent,
at a temperature of 220°-550° C.,
said catalyst being prepared by the following steps: a first step of preparing solutions of (A), (B) and (C), said (A) being an aqueous solution containing (a) a quaternary lower alkylammonium cation R, (b) an alkaline metal of sodium or potassium, and (c) and aqueous solution of a water soluble salt of a metal Me selected from the group consisting of B, Al, Ti, Zr, Ge, La, Mn, Cr, Sc, V, Fe, W, Mo, Co, Zn, Ga and Ni, (B) an aqueous silicate solution, and (C) an aqueous solution of an ion modifier, and adding the solution (A) and solution (B) to the solution (C) at a constant speed until a gelly mixture having a pH of around 10; a second step of grinding the resulting gel mixture; a third step of heating the gel mixture to a temperature of 150°–190° C. at a constant speed followed by heating to 220° C. at a constant speed or an exponential speed to obtain a precourser synthetic metallosilicate having the following chemical composition in molar ratio:

Si/Me: = 15–3500
$OH^-/SiO_2$: = 0.3–1.0
$H_2O/SiO_2$: = 30–100
R/(R+alkali metal): = 0.05–0.15
$NaCl/H_2O$: = 0.01–0.06 where R is a quaternary ammonium cation,
alkali metal is sodium or potassium,
Me is one metal ion of B, Al, Ti, V, Cr, Mn, Fe, Co, Ni, Zn, Ga, Ge, Zr, Mo, W, La or Sc, and fourth step of calcining the precourser.

2. A process according to claim 1 wherein the reaction is conducted under atmospheric pressure to 100 $Kg/cm^2$ and at space velocity of 300–15000 $hr^{-1}$.

3. A process according to claim 1 wherein the catalyst is that in which Me is Fe, B, W, Ni or Zn and acidity per g of catalyst is
total acid: 0.3–0.9 milli-equivalent
strong acid: 0.2–0.5 milli-equivalent
weak acid: 0.1–0.5 milli-equivalent.

4. A process according to claim 3 wherein the reaction is carried out at a temperature of 300°–550° C.

5. A process according to claim 3 wherein the reaction is carried out under atmospheric pressure to 50 $Kg/cm^2$ and at space velocity of 500–15000 $hr^{-1}$.

6. A process according to claim 1 wherein the catalyst is that in which Me is Ti, Ga, Mo, La, Al, Fe, W, B, Cr, Zn, Ni or Mn and acidity per g of catalyst is
total acid: 0.1–3.1 milli-equivalent
strong acid: 0.05–0.6 milli-equivalent
weak acid: 0.05–2.5 milli-equivalent.

7. A process according to claim 6 wherein the reaction is carried out at a temperature of 260°–400° C.

8. A process according to claim 6 wherein the reaction is carried out under atmospheric pressure to 100 $Kg/cm^2$ and at space velocity of 500–15000 $hr^{-1}$.

* * * * *